(12) United States Patent
Carlucci et al.

(10) Patent No.: US 8,969,651 B2
(45) Date of Patent: Mar. 3, 2015

(54) ABSORBENT CORE

(75) Inventors: Giovanni Carlucci, Chicti (IT); Andrea Peri, Sambuccto (IT); Maurizio Tamburro, Sambuccto (IT); Evelina Sara Toro, Chicti (IT)

(73) Assignee: The Procter & Gamble Company, Cincinnati, OH (US)

( * ) Notice: Subject to any disclaimer, the term of this patent is extended or adjusted under 35 U.S.C. 154(b) by 517 days.

(21) Appl. No.: 13/183,731

(22) Filed: Jul. 15, 2011

(65) Prior Publication Data

US 2013/0018341 A1  Jan. 17, 2013

(51) Int. Cl.
*A61F 13/15* (2006.01)

(52) U.S. Cl.
USPC .......... 604/378; 604/385.101; 604/367; 604/368; 604/374; 604/375; 604/365

(58) Field of Classification Search
USPC ........... 604/385.01, 378, 385.101, 367, 368, 604/374, 375, 365
See application file for complete search history.

(56) References Cited

U.S. PATENT DOCUMENTS

| | | | |
|---|---|---|---|
| 3,972,759 A * | 8/1976 | Buntin | 156/167 |
| 4,610,678 A * | 9/1986 | Weisman et al. | 604/368 |
| 7,744,576 B2 | 6/2010 | Busam et al. | |
| 7,750,203 B2 | 7/2010 | Becker et al. | |
| 7,851,667 B2 | 12/2010 | Becker et al. | |
| 2002/0102392 A1 | 8/2002 | Fish et al. | |
| 2004/0162536 A1 | 8/2004 | Becker et al. | |
| 2004/0167486 A1 | 8/2004 | Busam et al. | |
| 2007/0156108 A1 | 7/2007 | Becker et al. | |
| 2007/0167928 A1 | 7/2007 | Becker et al. | |
| 2007/0179464 A1 | 8/2007 | Becker et al. | |
| 2008/0125735 A1 | 5/2008 | Busam et al. | |
| 2009/0110998 A1 | 4/2009 | Miyachi et al. | |
| 2009/0287174 A1 | 11/2009 | Carlucci et al. | |
| 2010/0036342 A1 | 2/2010 | Carlucci et al. | |
| 2010/0228210 A1 | 9/2010 | Busam et al. | |
| 2010/0228211 A1 | 9/2010 | Becker et al. | |
| 2010/0239946 A1 | 9/2010 | Miyachi et al. | |
| 2010/0262104 A1 * | 10/2010 | Carlucci et al. | 604/366 |
| 2011/0130734 A1 * | 6/2011 | Carlucci et al. | 604/369 |

FOREIGN PATENT DOCUMENTS

EP  1447067 B1  12/2007

OTHER PUBLICATIONS

International Search Report, mailed Sep. 20, 2011, 4 pages.
PCT Search Report, mailed Sep. 20, 2011, 10 pages.

* cited by examiner

*Primary Examiner* — Jacqueline F. Stephens
(74) *Attorney, Agent, or Firm* — Andres E. Velarde; Brian M. Bolam

(57) ABSTRACT

An absorbent core structure for disposable absorbent articles, having improved fluid handling properties.

24 Claims, 4 Drawing Sheets

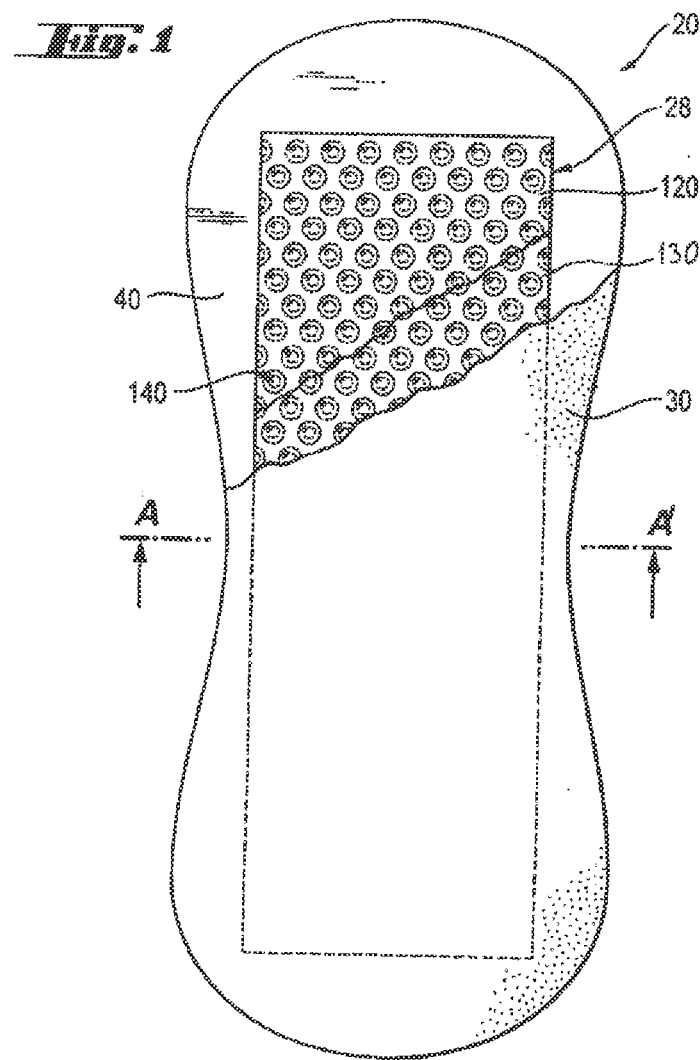
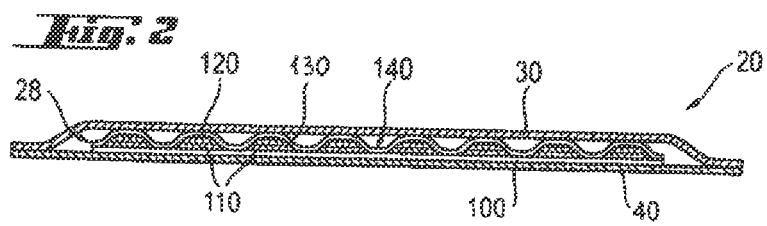

ABSORBENT CORE

FIELD OF THE INVENTION

The present invention relates to an absorbent core structure for absorbent articles, for example sanitary napkins and the like.

BACKGROUND OF THE INVENTION

Absorbent articles for absorption of body fluids such as menses or blood or vaginal discharges are well known in the art, and comprise for example feminine hygiene articles such as sanitary napkins, panty liners, tampons, interlabial devices, as well as wound dressings, and the like. When considering for example sanitary napkins, these articles typically comprise a liquid-pervious topsheet as wearer-facing layer, a backsheet as garment-facing layer and an absorbent structure, also referred to as core, between topsheet and backsheet. The body fluids are acquired through the topsheet and subsequently stored in the absorbent core structure. The backsheet typically prevents the absorbed fluids from wetting the wearer's garment.

An absorbent core structure can typically comprise one or more fibrous absorbent materials, which in turn can comprise natural fibres, such as for example cellulose fibres, typically wood pulp fibres, synthetic fibres, or combinations thereof.

Absorbent articles can further comprise, typically in the absorbent core, superabsorbent materials, such as absorbent gelling materials (AGM), usually in finely dispersed form, e.g. typically in particulate form, in order to improve their absorption and retention characteristics. Superabsorbent materials for use in absorbent articles typically comprise water-insoluble, water-swellable, hydrogel-forming crosslinked absorbent polymers which are capable of absorbing large quantities of liquids and of retaining such absorbed liquids under moderate pressure. Absorbent gelling materials can be incorporated in absorbent articles, typically in the core structure, in different ways; for example, absorbent gelling materials in particulate form can be dispersed among the fibres of fibrous layers comprised in the core, or rather localized in a more concentrated arrangement between fibrous layers.

Absorbent cores for absorbent articles having a thin structure can further provide an improved immobilization of absorbent gelling materials, particularly when the article is fully or partially loaded with liquid, and an increased wearing comfort. Such thinner structures provide absorbent articles combining better comfort, discreetness and adaptability, such as for example, thin absorbent structures where the absorbent gelling material is located and somehow kept in selected, e.g. patterned regions of the structure itself.

EP 1447067, assigned to the Procter & Gamble Company, describes an absorbent article, typically a disposable absorbent article, such as a diaper, having an absorbent core which imparts increased wearing comfort to the article and makes it thin and dry. The absorbent core comprises a substrate layer, the substrate layer comprising a first surface and a second surface, the absorbent core further comprising a discontinuous layer of absorbent material, the absorbent material comprising an absorbent polymer material, the absorbent material optionally comprising an absorbent fibrous material which does not represent more than 20 weight percent of the total weight of the absorbent polymer material. The discontinuous layer of absorbent material comprises a first surface and a second surface, the absorbent core further comprising a layer of thermoplastic material, the layer of thermoplastic material comprising a first surface and a second surface and wherein the second surface of the discontinuous layer of absorbent material is in at least partial contact with the first surface of the substrate layer and wherein portions of the second surface of the layer of thermoplastic material are in direct contact with the first surface of the substrate layer and portions of the second surface of the layer of thermoplastic material are in direct contact with the first surface of the discontinuous layer of absorbent material.

Absorbent articles according to EP 1447067 and comprising thin absorbent cores with relatively high amounts of absorbent gelling materials and rather low content of fibrous materials commonly have good absorption and retention characteristics to body fluids. However there still remains room for improvement for fluid handling, and particularly in order to better control rewet, e.g. due to gushing, and fluid acquisition effectiveness, in a core structure which is thin and comfortable, yet highly absorbent.

Low rewet, i.e. the capability of an absorbent structure of effectively and stably entrapping fluid within the structure itself, even after e.g. sudden gushes, with low tendency to give it back upon compression, for example upon squeezing of the absorbent structure which may occur during wear, is typically a characteristic which is in contrast with fast fluid acquisition, particularly in a thin absorbent structure. In other words, in order to have a thin absorbent structure which is also highly absorbent it is typically necessary to compromise between these two apparently contrasting features. In fact a thin absorbent structure, in order to rapidly acquire fluid, can typically have a rather "open" structure, which may in turn not provide for an optimal low rewet.

Thus, an absorbent core structure is desired exhibiting thinness for comfort combined with high absorbent capacity, while at the same time providing low rewet and fast fluid acquisition.

SUMMARY OF THE INVENTION

The present invention addresses the above need by providing an absorbent core structure for an absorbent article, which comprises a first layer, comprising a first surface and a second surface; the absorbent core further comprises a layer of absorbent polymer material, comprising a first surface and a second surface; the absorbent core also comprises a layer of adhesive, comprising a first surface and a second surface. The layer of absorbent polymer material is comprised between the layer of adhesive material and the first layer. The second surface of the layer of absorbent polymer material is facing the first surface of the first layer, and the first surface of the layer of absorbent polymer material is facing the second surface of the layer of adhesive. The absorbent core structure of the present invention further comprises a second layer having respective first and second surface, positioned such that the second surface of the second layer is facing the first surface of the layer of adhesive.

The first layer of the absorbent core structure has a thickness of 0.4 mm to 1.5 mm, and the second layer of the absorbent core structure has a permeability of at least 200 Darcy, and a porosity of at least 0.85.

BRIEF DESCRIPTION OF THE DRAWINGS

FIG. 1 is a plan view of a sanitary napkin showing an absorbent core according to an embodiment of the present invention, with portions of some constituent elements cut out in order to show underlying elements.

FIG. 2 is a schematic cross section of the sanitary napkin of FIG. 1 taken in the transverse axis A-A'.

DETAILED DESCRIPTION OF THE INVENTION

Figure 3:
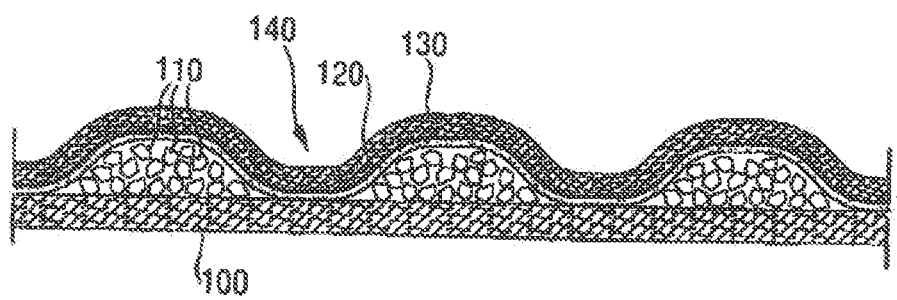
FIG. 3 shows a schematic cross section of an absorbent core according to one embodiment of the present invention.

The present invention relates to an absorbent core for absorbent articles such as sanitary napkins, panty liners, tampons, interlabial devices, wound dressings, diapers, adult incontinence articles, and the like, which are intended for the absorption of body fluids, such as menses or blood or vaginal discharges or urine. Exemplary absorbent articles in the context of the present invention are disposable absorbent articles. The term "disposable" is used herein to describe articles, which are not intended to be laundered or otherwise restored or reused as an article (i.e. they are intended to be discarded after a single use and possibly to be recycled, composted or otherwise disposed of in an environmentally compatible manner). The terms "absorbent core" and "absorbent core structure" as used herein, are interchangeable, and refer to the core of the absorbent article. The absorbent article comprising an absorbent core according to the present invention can be for example a sanitary napkin or a panty liner. The absorbent core of the present invention will be herein described in the context of a typical absorbent article, such as, for example, a sanitary napkin 20 as illustrated in FIG. 1. Typically, such articles as shown in FIG. 1 can comprise the elements of a liquid pervious topsheet 30, a backsheet 40 and an absorbent core 28 intermediate said topsheet 30 and said backsheet 40.

In the following description of the invention, the surface of the article, or of each element thereof, which in use faces in the direction of the wearer is called wearer-facing surface. Conversely, the surface facing in use in the direction of the garment is called garment-facing surface. The absorbent article of the present invention, as well as any element thereof, such as, for example the absorbent core, has therefore a wearer-facing surface and a garment-facing surface.

Topsheet

According to the present invention, the absorbent article can comprise a liquid pervious topsheet. The topsheet suitable for use herein can comprise wovens, non-wovens, and/or three-dimensional webs of a liquid impermeable polymeric film comprising liquid permeable apertures. In FIG. 1 the topsheet is indicated with reference numeral 30. The topsheet for use herein can be a single layer or may have a multiplicity of layers. For example, the wearer-facing and contacting surface can be provided by a film material having apertures which are provided to facilitate liquid transport from the wearer facing surface towards the absorbent structure. Such liquid permeable, apertured films are well known in the art. They provide a resilient three-dimensional fibre-like structure. Such films have been disclosed in detail for example in U.S. Pat. Nos. 3,929,135, 4,151,240, 4,3198,68, 4,324,426, 4,343,314, 4,591,523, 4,609,518, 4,629,643, 4,695,422 or WO 96/00548.

Absorbent Core

Figure 4:
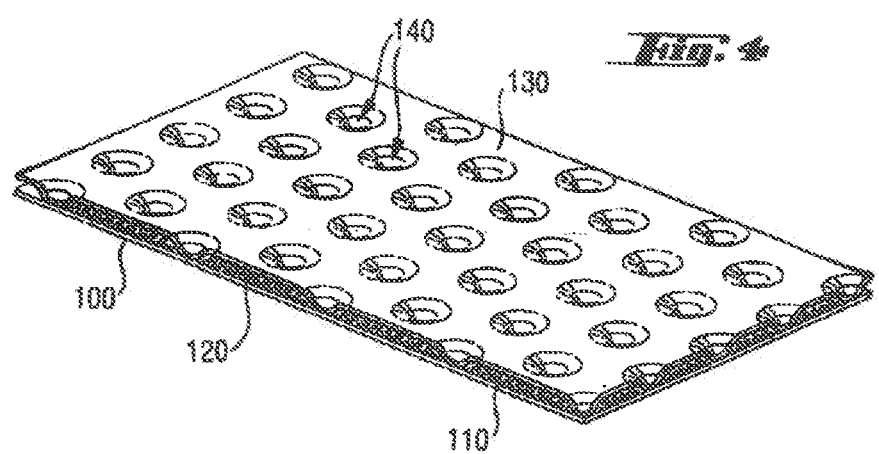
FIG. 4 shows a perspective view of an exemplary absorbent core according to the present invention.

According to the present invention, and as shown for example in the embodiments of FIGS. 3 and 4, the absorbent core 28 can comprise a first layer, or substrate layer, 100, a layer of absorbent polymer material 110, a layer of adhesive 120, and a second layer, or cover layer, 130. According to the present invention, in the following description the terms "first layer" and "second layer" can be used interchangeably with "substrate layer" and "cover layer" respectively, and are meant to respectively refer to layers 100 and 130 in FIG. 3. The terms "substrate" and "cover", referred to the first layer 100 and to the second layer 130, reflect one possible orientation of the absorbent core structure 28 when for example incorporated into an absorbent article, such as for example the sanitary napkin 20 shown in FIG. 1, wherein the first layer 100 can actually constitute a substrate layer in that it is a bottom layer, i.e. for example closer to the backsheet 40, and the second layer 130 can actually constitute a cover layer in that it is a top layer, i.e. closer to the topsheet 30. Typically the adhesive can be a hot melt adhesive. According to the present invention, the layer of adhesive 120 can be typically for example a layer of fiberized hot melt adhesive 120. The substrate layer 100 can for example comprise a fibrous material. Suitable materials for the cover layer can be for example nonwoven materials.

The substrate layer 100, the layer of absorbent polymer material 110, the layer of adhesive 120, and the cover layer 130 each comprise a first surface and a second surface. Conventionally, in all the sectional views illustrated in the attached drawings the first surface of each layer is meant to correspond to the top surface, in turn, unless stated otherwise, corresponding to the wearer facing surface of the article 20 incorporating the absorbent core, while the second surface corresponds to the bottom surface, hence in turn the garment facing surface.

In general, in the absorbent core structure 28 of the present invention the arrangement of the various layers is such that the second surface of the layer of absorbent polymer material 110 is facing the first surface of the first or substrate layer 100, the first surface of the layer of absorbent polymer material 110 is facing the second surface of the layer of adhesive 120, and the second surface of the second or cover layer 130 is facing the first surface of the layer of adhesive 120.

According to the present invention, at least portions of the first surface of the substrate layer 100 can be in contact with the layer of absorbent polymer material 110. This layer of absorbent polymer material 110 comprises a first surface and a second surface, and can be typically a uniform or non uniform layer, wherein by "uniform" or "non uniform" it is meant that the absorbent polymer material 110 can be distributed over the substrate layer 100 respectively with uniform or non uniform basis weight over the area interested by the distribution. Conversely, the second surface of the layer of absorbent polymer material 110 can be in at least partial contact with the first surface of the substrate layer 100. According to the present invention, the layer of absorbent polymer material 110 can also be a discontinuous layer that is a layer typically comprising openings, i.e. areas substantially free of absorbent polymer material, which in certain embodiments can be typically completely surrounded by areas comprising absorbent polymer material. Typically these openings have a diameter or largest span of less than 10 mm, or less than 5 mm, or 3 mm, or 2 mm, or 1.5 mm and of more than 0.5 mm, or 1 mm. At least portions of the second surface of the absorbent polymer material layer 110 can be in contact with at least portions of the first surface of the substrate layer material 100. The first surface of the layer of absorbent polymer material 110 defines a certain height of the layer of absorbent polymer material above the first surface of the layer of substrate material 100. When the absorbent polymer material layer 110 is provided as a non uniform layer, typically for example as a discontinuous layer, at least some portions of the first surface of the substrate layer 100 can be not covered by absorbent polymer material 110. The absorbent core 28 further comprises a layer of adhesive 120, for example typically a hot melt adhesive. This typically hot melt adhesive 120 serves to at least partially immobilize the absorbent polymer material 110. According to the present invention, the adhesive 120 can be typically a fiberized hot melt adhesive, i.e., being provided in fibres as a fibrous layer.

The absorbent core 28 comprises a cover layer 130 having respective first and second surface, positioned such that the second surface of the cover layer 130 can be in contact with the first surface of the layer of typically hot melt adhesive 120.

According to the present invention comprising e.g. a non uniform layer of absorbent polymer material 110 the typically hot melt adhesive 120, for example typically provided as a fibrous layer, can be partially in contact with the absorbent polymer material 110 and partially in contact with the substrate layer 100. FIGS. 3 and 4 show such a structure in an exemplary embodiment of the present invention. In this structure the absorbent polymer material layer 110 is provided as a discontinuous layer, a layer of adhesive 120 is laid down onto the layer of absorbent polymer material 110, typically, for example, a layer of hot melt adhesive in fiberized form, such that the second surface of the adhesive layer 120 can be in direct contact with the first surface of the layer of absorbent polymer material 110, but also in direct contact with the first surface of the substrate layer 100, where the substrate layer is not covered by the absorbent polymer material 110, i.e. typically in correspondence of the openings of the discontinuous layer of the absorbent polymer material 110. By saying "in direct contact", as well as more generally "in contact", as used herein, in contrast to more generally saying "facing", it is meant that there is no further intermediate component layer between e.g. the layer of adhesive 120 and the other respective layer in direct contact thereto, such as for example a further fibrous layer. It is however not excluded that a further adhesive material can be comprised between the layer of adhesive 120 and the cover layer 130, or the layer of absorbent polymer material 110 or, more typically, the substrate layer 100, such as for example a supplementary adhesive material provided onto the first surface of the substrate layer 100 to further stabilize the overlying absorbent polymer material 110. "In direct contact" and "in contact" can hence be considered to comprise in this context a direct adhesive contact between the layer of hot melt adhesive 120 and another respective layer as explained above, or more in general direct and, typically, adhesive contact between two layers, e.g. the layer of absorbent polymer material and the substrate layer. This imparts an essentially three-dimensional structure to the fibrous layer of hot melt adhesive 120 which in itself is essentially a two-dimensional structure of relatively small thickness (in z-direction), as compared to the extension in x- and y-direction. In other words, the layer of adhesive 120 undulates between the first surface of the absorbent polymer material 110 and the first surface of the substrate layer 100. The areas where the layer of adhesive 120 is in direct contact with the substrate layer 100, when present according to an embodiment of the present invention, are the areas of junction 140.

Thereby, in such an embodiment the adhesive 120 can provide spaces to hold the absorbent polymer material 110 typically towards the substrate layer 100, and can thereby immobilize this material. In a further aspect, the adhesive 120 can bond to the substrate 100 thus affixing the absorbent polymer material 110 to the substrate 100. Typical hot melt adhesive materials can also penetrate into both the absorbent polymer material 110 and the substrate layer 100, thus providing for further immobilization and affixation.

In the embodiment of FIG. 3 portions of the cover layer 130 bond to portions of the substrate layer 100 via the adhesive 120. Thereby, the substrate layer 100 together with the cover layer 130 can provide spaces to immobilize the absorbent polymer material 110.

Of course, while the typically hot melt adhesive materials disclosed herein can provide a much improved wet immobilisation, i.e. immobilisation of absorbent polymer material when the article is wet or at least partially loaded, these hot melt adhesive materials can also provide a very good immobilisation of absorbent polymer material when the article is dry.

In accordance with the present invention, the absorbent polymer material 110 may also be optionally mixed with fibrous material, which can provide a matrix for further immobilization of the absorbent polymer material. However, typically a relatively low amount of fibrous material can be used, for example less than about 40 weight %, less than about 20 weight %, or less than about 10 weight % of the total weight of the absorbent polymer material 110, positioned within the areas of absorbent polymer material.

According to the present invention, in a typically discontinuous layer of absorbent polymer material 110 the areas of absorbent polymer material can be connected to one another, while the areas of junction 140 can be areas, which in an embodiment may correspond to the openings in the discontinuous layer of absorbent polymer material, as shown for example in FIG. 4. The areas of absorbent polymer material are then referred to as connected areas. In an alternative embodiment, the areas of junction 140 can be connected to one another. Then, the absorbent polymer material can be deposited in a discrete pattern, or in other words the absorbent polymer material represents islands in a sea of adhesive 120. Hence, in summary, a discontinuous layer of absorbent polymer material 110 may comprise connected areas of absorbent polymer material 110, as e.g. illustrated in FIG. 4, or may alternatively comprise discrete areas of absorbent polymer material 110.

The present invention, and for example the embodiments described with reference to FIGS. 3 and 4 can be typically used to provide the absorbent core of an absorbent article, as illustrated in FIG. 1. In that case, no further materials wrapping the core, such as for example a top layer and a bottom layer are being used. With reference to the embodiment of FIG. 3 the optional cover layer 130 may provide the function of a top layer and the substrate layer 100 may provide the function of a bottom layer of an absorbent core, wherein top and bottom layers respectively correspond to the body facing and garment facing surfaces of the core 28 in an absorbent article.

With reference to FIGS. 3 and 4, according to exemplary embodiments of the present invention, the areas of direct contact between the adhesive 120 and the substrate material 100 are referred to as areas of junction 140. The shape, number and disposition of the areas of junction 140 will influence the immobilization of the absorbent polymer material 110. The areas of junction can be for example of squared, rectangular or circular shape. Areas of junction of circular shape can have a diameter of more than 0.5 mm, or more than 1 mm, and of less than 10 mm, or less than 5 mm, or less than 3 mm, or less than 2 mm, or less than 1.5 mm. If the areas of junction 140 are not of circular shape, they can be of a size as to fit inside a circle of any of the diameters given above.

The areas of junction 140, when present, can be disposed in a regular or irregular pattern. For example, the areas of junction 140 may be disposed along lines as shown in FIG. 4. These lines may be aligned with the longitudinal axis of the absorbent core, or alternatively they may have a certain angle in respect to the longitudinal edges of the core. A disposition along lines parallel with the longitudinal edges of the absorbent core 28 might create channels in the longitudinal direction which can lead to a lesser wet immobilization, hence for example the areas of junction 140 can be arranged along lines which form an angle of about 20 degrees, or about 30 degrees, or about 40 degrees, or about 45 degrees with the longitudinal edges of the absorbent core 28. Another pattern for the areas of junction 140 can be a pattern comprising polygons, for example pentagons and hexagons or a combination of pentagons and hexagons. Also typical can be irregular patterns of areas of junction 140, which also can give a good wet immobilization. Irregular patterns of areas of junction 140 can also give a better fluid handling behaviour in case of absorption of menses or blood or vaginal discharges, since fluid can start diffusing in whichever direction from any initial acquisition point with substantially the same probability of contacting the absorbent polymer material in the e.g. discontinuous layer. Conversely, regular patterns might create preferential paths the fluid could follow with lesser probability of actually contacting the absorbent polymer material.

According to the present invention the layer of adhesive 120 can comprise any suitable adhesive material. Typically, the layer of adhesive 120 can comprise any suitable hot melt adhesive material.

Without wishing to be bound by theory it has been found that those hot melt adhesive materials can be most useful for immobilizing the absorbent polymer material 110, which combine good cohesion and good adhesion behaviour. Good adhesion can typically ensure that the hot melt adhesive layer 120 maintains good contact with the absorbent polymer material 110 and in particular with the substrate material 100. Good adhesion is a challenge, namely when a nonwoven substrate material is present. Good cohesion ensures that the adhesive does not break, in particular in response to external forces, and namely in response to strain. The adhesive is subject to external forces when the absorbent product has acquired liquid, which is then stored in the absorbent polymer material 110 which in response swells. An exemplary adhesive should allow for such swelling, without breaking and without imparting too many compressive forces, which would restrain the absorbent polymer material 110 from swelling. It may be desirable that the adhesive does not break, which would deteriorate the wet immobilization. Exemplary suitable hot melt adhesive materials can be as described in the already mentioned patent application EP 1447067, particularly at sections [0050] to [0063].

The adhesive material, typically a hotmelt adhesive material, can be typically present in the form of fibres throughout the core, being provided with known means, i.e. the typically hot melt adhesive can be fiberized. Typically, the fibres can have an average thickness from about 1 μm to about 100 μm, or from about 25 μm to about 75 μm, and an average length from about 5 mm to about 50 cm. In particular the layer of typically hot melt adhesive material can be provided such as to comprise a net-like structure.

According to the present invention, the adhesive material constituting the layer of adhesive 120, typically a hot melt adhesive, may have a basis weight of from 11 g/m² to 3 g/m², preferably of from 9 g/m² to 5 g/m², for example 8 g/m², or 6 g/m².

To improve the adhesiveness of the typically hot melt adhesive material 120 to the substrate layer 100 or to any other layer, in particular any other non-woven layer, such layers may be pre-treated with an auxiliary adhesive.

In particular, typical parameters of a hot melt adhesive in accordance with the present invention can be as follows.

In an aspect, the loss angle tan Delta of the adhesive at 60° C. should be below the value of 1, or below the value of 0.5. The loss angle tan Delta at 60° C. is correlated with the liquid character of an adhesive at elevated ambient temperatures. The lower tan Delta, the more an adhesive behaves like a solid rather than a liquid, i.e. the lower its tendency to flow or to migrate and the lower the tendency of an adhesive superstructure as described herein to deteriorate or even to collapse over time. This value is hence particularly important if the absorbent article is used in a hot climate.

In a further aspect, typical hot melt adhesives in accordance with the present invention may have a sufficient cohesive strength parameter γ. The cohesive strength parameter γ is measured using the Rheological Creep Test as referred to hereinafter. A sufficiently low cohesive strength parameter γ is representative of elastic adhesive which, for example, can be stretched without tearing. If a stress of τ=1000 Pa is applied, the cohesive strength parameter γ can be less than 100%, less than 90%, or less than 75%. For a stress of τ=125000 Pa, the cohesive strength parameter γ can be less than 1200%, less than 1000%, or less than 800%.

It is believed that the layer of adhesive 120, typically a hot melt adhesive, provided onto the layer of absorbent polymer material 110, and in direct contact therewith, can provide an effective absorbent structure, stabilizing and containing the absorbent polymer material onto the substrate layer 100, both in dry, and also in wet conditions. This can be particularly relevant when the layer of absorbent polymer material 110 is provided by absorbent polymer particles, wherein the occurrence of loose absorbent polymer particles within the absorbent core structure is minimized.

Materials

Exemplary materials for the substrate layer 100 according to the present invention can comprise nonwoven materials comprising synthetic fibres, or natural fibres, or mixtures thereof, such as for example carded nonwovens, or more typically airlaid or wetlaid fibrous materials. The substrate layer 100 according to the present invention can be selected for example among latex or thermal bonded airlaid fibrous materials, comprising synthetic fibres and 0 to 50% by weight, or 0 to 20% by weight natural fibres, such as for example cellulose fibres.

According to another embodiment of the present invention, the substrate layer 100 can comprise a fibrous material comprising cellulose or cellulose derivative fibres, for example from about 40% to about 100% by weight of cellulose or cellulose derivative fibres, or from about 50% to about 95% by weight of cellulose or cellulose derivative fibres, or also from about 60% to about 90% by weight of cellulose or cellulose derivative fibres. In a core structure according to the present invention a substrate layer 100 constituted by a fibrous material comprising a substantial percentage of cellulose fibres can provide an advantage in terms of liquid distribution towards the liquid fraction which is not immediately absorbed by the upper layer of absorbent polymer material 110, and is directly acquired by the substrate layer 100.

According to the present invention, basis weights for the first or substrate layer 100 can typically range from about 10 g/m² to about 120 g/m², or from about 20 g/m² to about 100 g/m², or also from about 30 g/m² to about 70 g/m².

Exemplary materials for the cover layer 130 can be provided by nonwoven materials comprising synthetic fibres, such as polyethylene (PE), polyethylene terephthalate (PET), polypropylene (PP), and cellulose or cellulose derivative fibres. Exemplary materials can comprise for example from about 0% to about 90% by weight of cellulose or cellulose derivative fibres, or from about 50% to about 85% by weight of cellulose or cellulose derivative fibres, or also from about 60% to about 80% by weight of cellulose or also typically cellulose derivative fibres. As the synthetic polymers used for nonwoven production are usually inherently hydrophobic, they can be typically coated with hydrophilic coatings, for example with durably hydrophilic coatings to provide permanently hydrophilic nonwovens. Other nonwoven materials for the cover layer 130 can comprise composite structures such as a so called SMS material, comprising a spunbonded, a melt-blown and a further spunbonded layer. Basis weights for the second or cover layer 130 according to the present invention can typically range from 10 $g/m^2$ to 80 $g/m^2$, or from 10 $g/m^2$ to 60 $g/m^2$, or also from 20 m $g/m^2$ to 40 $g/m^2$.

Typically the absorbent polymer material 110 for the absorbent cores according to the present invention can comprise absorbent polymer particles, known in the art e.g. as superabsorbent materials, or as absorbent gelling materials (AGM), or also as hydrogel forming materials, as referred to in the Background of the Invention. Typically absorbent polymer particles can have a selected average particle size.

According to the present invention, absorbent polymer materials, typically in particle form, can be selected among polyacrylates and polyacrylate based materials, such as for example partially neutralized, crosslinked polyacrylates.

According to the present invention the layer of absorbent polymer material 110 in the absorbent core 28 can be present throughout the area of the absorbent core in an average basis weight of less than 250 $g/m^2$, or of less than about 200 $g/m^2$, or from about 60 $g/m^2$ to about 180 $g/m^2$, or from about 70 $g/m^2$ to about 150 $g/m^2$. An average basis weight is typically based on the whole area of the zone of application, i.e. interested by the layer of absorbent polymer material, and hence comprising possible openings included in an e.g. discontinuous layer. Typically, the absorbent polymer material 110 can constitute at least about 45%, or at least about 50%, or at least about 55%, by weight of the absorbent core, wherein the absorbent core can typically correspond to the embodiments described with reference to FIGS. 3 and 4, hence comprising the substrate layer, the layer of absorbent polymer material, the layer of thermoplastic material, the cover layer, and any other material possibly comprised within this structure as described above, namely for example the additional fibrous material mentioned above or the additional adhesive material.

The absorbent polymer particles of the layer of absorbent polymer material 110, can typically have a selected average particle size from about 200μ to about 600μ, or from about 300μ to about 500μ.

The average particle size of a material in particulate form, namely for example the absorbent polymer material, can be determined as it is known in the art, for example by means of dry sieve analysis. Optical methods, e.g. based on light scattering and image analysis techniques, can also be used.

According to the present invention the absorbent polymer material, typically e.g. in particle form, can be selected among the polyacrylate based polymers described in the PCT Patent Application WO 07/047598, which are polyacrylate based materials very slightly crosslinked, or substantially not crosslinked at all, this further improving the above mentioned synergistic effect. Particularly, said polyacrylate based materials can have an extractable fraction of at least about 30% by weight, between about 30% and about 80% by weight, or between about 32% and about 70% by weight, evaluated according to the Extractables test method described in the above referenced application. Alternatively, said polyacrylate based materials can have a retention capacity of at least about 30 g/g, at least about 35 g/g, or at least about 40 g/g, evaluated according to the Centrifuge Retention Capacity test described in the above referenced application. The absorbent polymer material can also be selected among the polyacrylate based polymers described in the PCT Patent Application WO 07/046052. Said polymers in fact are particularly effective in absorbing complex body fluids such as menses or blood, and upon absorption of such fluids do not generally show a marked swelling, followed by gel blocking, like traditional superabsorbents, but rather act to a certain extent as thickeners of the body fluid, immobilizing it as a sort of gelatinous mass within the absorbent structure, for example in the interstices among the fibres, without causing substantial swelling and in turn a sensible increase of the overall thickness of the absorbent core.

According to the present invention, the absorbent core can provide a more efficient fluid management, in terms of acquisition, immobilization and absorption and a better comfort, during the entire wearing time of the article, as explained above, which can be particularly useful in case of complex body fluids such as menses or blood. Overall, this increased efficiency in the composite structure according to the present invention can translate in a more effective exploitation of the absorbent capacity of the absorbent polymer material, also in presence of problematic body fluids such as menses or blood or vaginal discharges, and possibly also in a more efficient use of the entire structure of the absorbent core.

This is achieved in a structure which is typically thin and flexible, yet capable of employing more completely the absorption and immobilization capacity of the different materials, and having improved fit and resilience during absorption and therefore increased comfort during use.

According to the present invention, the absorbent core structure 28 can be constituted by the layers 100, 110, 120, and 130 described above, or can comprise additional layers. For example, an absorbent article can comprise an absorbent core according to the present invention further comprising a fibrous acquisition layer, for example between the second or cover layer 130 and the topsheet. According to the present invention the acquisition layer can for example comprise fibrous nonwoven materials made by air laying or wet laying of synthetic fibres such as polyethylene (PE), polyethylene terephthalate (PET), or polypropylene (PP), similarly to the cover layer 130 of the absorbent core 28 of the present invention.

Exemplary materials for the fluid acquisition layer could comprise spunbonded or carded nonwoven materials, or airlaid materials such as for example latex bonded or thermal bonded airlaid materials. Basis weights can typically range from about 10 $g/m^2$ to about 60 $g/m^2$, or from about 25 $g/m^2$ to about 40 $g/m^2$.

According to another embodiment of the present invention the absorbent article can comprise a further fibrous layer comprised for example between the first or substrate layer 100 and the backsheet, i.e. typically provided at the garment facing surface of the core. This optional layer can be provided by similar fibrous materials as those already described for the substrate layer 100 of the absorbent core of the present invention. This optional fibrous layer according to this further embodiment of the present invention can act as an added wicking layer receiving and distributing excess fluid. The presence of cellulose fibres can make the layer particularly effective in acquiring and diffusing the fraction of body fluids like menses or blood which is not completely absorbed by the absorbent polymer material of the absorbent core 28.

Further materials, also typically in particle form, can be comprised in the layer of absorbent polymer material, for example known odour control materials, or inert materials such as silica.

Backsheet

The absorbent article of FIG. 1 comprising the absorbent core according to the present invention can also comprise a backsheet 40. The backsheet may be used to prevent the fluids absorbed and contained in the absorbent structure from wetting materials that contact the absorbent article such as underpants, pants, pyjamas, undergarments, and shirts or jackets, thereby acting as a barrier to fluid transport. The backsheet according to the present invention can also allow the transfer of at least water vapour, or both water vapour and air through it.

Especially when the absorbent article finds utility as a sanitary napkin or panty liner, the absorbent article can be also provided with a panty fastening means, which provides means to attach the article to an undergarment, for example a panty fastening adhesive on the garment facing surface of the backsheet. Wings or side flaps meant to fold around the crotch edge of an undergarment can be also provided on the side edges of the napkin.

In the present invention, the absorbent core structure can be provided by appropriately selecting its components, and particularly typically the substrate layer, the absorbent polymer material, and the cover layer, in order to improve its fluid handling properties. In a thin absorbent structure as that of the present invention, a high fluid acquisition capacity and a low rewet are two characteristics which are most beneficial to the user, as they ultimately provide for an absorbent product, comprising the absorbent core structure of the invention, which promptly acquires and absorbs fluid, also after sudden gushes, and effectively retains it also under pressure, typically for example when the article is squeezed and to a certain extent deformed by the forces exerted by the body during wear. Rewet of an absorbent structure, as known in the art, corresponds to the tendency of the absorbent structure to give back fluid after its absorption when subjected to compression, and can be measured according to appropriate tests. Hence rewet can be a measure of how effectively absorbed fluid is entrapped within an absorbent structure, and a low rewet generally corresponds to a better capacity of the absorbent structure of holding fluid, and of ultimately providing an absorbent article which can have a less wet, hence a drier surface and thus be more comfortable to the wearer. Typically in an absorbent structure a high fluid acquisition capacity, i.e. namely the capacity of acquiring fluid quickly within the structure, also when provided as a sudden gush, can be associated to a relative openness of the absorbent structure itself, which in turn can be less than optimal for rewet. Hence a high fluid acquisition capacity and a low rewet, though most beneficial for an absorbent structure, can be considered as contrasting features of an absorbent structure, particularly for a thin absorbent structure which can be preferred for comfort and discreetness, for which so far it has been necessary to compromise.

It has been now discovered that, by suitably selecting the component elements of an absorbent structure of the present invention it is possible to achieve both low rewet and high fluid acquisition capacity, moreover in an absorbent structure which is also particularly thin.

The performances of an absorbent structure in terms of fluid acquisition capacity and rewet can be measured according to appropriate test methods described herein. In particular, the fluid acquisition capacity is measured as the acquisition time of the absorbent structure after provision of multiple gushes of fluid at different times; it has been found that the acquisition time after the third gush, according to the test method described herein, can be considered representative of the capability of the absorbent core structure of effectively receiving subsequent amounts of fluid in an already wet condition, i.e. after a certain amount of fluid has been already acquired.

According to the present invention, the component elements of an absorbent core structure as that illustrated in FIG. 3 may be suitably selected in order to have certain characteristics, expressed in terms of certain selected parameters which are used to represent them. According to the present invention, the parameters are Permeability, Porosity and Thickness, as will be explained more in detail. Generally speaking, Permeability may be considered in the context of the present invention as representative of the capability of a given material to transmit fluid in the x-y plane, while Porosity can be considered as representative of the void volume fraction of a material, typically available for absorption of fluid.

An absorbent core structure according to the present invention, for example as illustrated in FIG. 3, can have a second or cover layer 130 with a Permeability of at least 200 Darcy, or at least 250 Darcy, or also at least 300 Darcy. According to the present invention, the Permeability of the second or cover layer 130 can be up to 500 Darcy, or up to 600 Darcy. According to the present invention the cover layer 130 may be selected in order to have a Porosity of at least 0.85, or typically of 0.85 to 0.95, or also of 0.87 to 0.90.

The substrate or first layer 100 of an absorbent core structure according to the present invention may be selected such as to have a thickness of 0.4 mm to 1.5 mm, or typically of 0.5 mm to 1.2 mm.

The overall thickness of the absorbent core structure according to the present invention can be of 0.5 mm to 2.5 mm, or of 1 mm to 2 mm, hence providing an absorbent structure having the desired characteristics of fluid acquisition and rewet in a very thin structure, owing to the appropriate selection of the component materials according to the criteria illustrated in the present invention.

Porosity, Permeability and Thickness are measured for the respective layers according to the test methods described herein.

The overall basis weight of an absorbent structure according to the present invention can be of 90 $g/m^2$ to 400 $g/m^2$, or of 100 $g/m^2$ to 350 $g/m^2$, or also of 130 $g/m^2$ to 270 $g/m^2$.

The absorbent core structure according to the present invention shall comprise at least the first and the second layer 100, 130, the layer of absorbent polymer material 110 and the layer of adhesive 120, as described herein, and in an embodiment of the present invention can be actually constituted by the above layers. According to the present invention the absorbent core structure can also comprise other layers, as already explained. For example, the absorbent core structure comprised between the topsheet and the backsheet can further comprise additional layers such as an acquisition layer and/or a distribution layer, respectively positioned for example between the cover layer 130 and the topsheet 30, or between the substrate layer 100 and the backsheet 40.

The invention will be illustrated with the following examples, where absorbent core structures are described having a first layer or substrate layer 100 corresponding, when the absorbent core structure is incorporated within an absorbent core product, such as for example typically a sanitary napkin, to a garment-facing surface of the structure itself, while the second or cover layer 130 corresponds to the wearer-facing surface.

An absorbent core as that illustrated in FIG. 3 comprises a first layer or substrate layer 100 constituted by a 65 g/m² Latex Bonded AirLaid (LBAL) fibrous layer constituted by a homogeneous blend of 16 g/m² polyethylene terephthalate (PET), 6.7 dtex, 6 mm long fibres and 19.5 g/m² pulp fibres laid onto a 10 g/m² spunbonded polypropylene nonwoven, with 19.5 g/m² latex, having a thickness of 0.7 mm, identified as material "D" in Table 1, a layer of absorbent polymer material 110 constituted by a particulate superabsorbent material available from Nippon Shokubai under the trade name Aqualic L520 distributed onto the substrate layer in a uniform layer having overall an average basis weight of 144 g/m², a layer of adhesive material 120 constituted by a hot melt adhesive available from HB Fuller under the trade name NV 1151 Zeropack applied in fibres having an average thickness of about 50 μm at a basis weight of 8 g/m², the layers 110 and 120 having an overall thickness of 0.5 mm, and a second layer or cover layer 130 constituted by a 28 g/m² hydrophilic spunbonded nonwoven of bicomponent 80/20 core/sheath polypropylene/polyethylene (PP/PE) fibres, treated with 0.5% by weight Silastol PHP26 surfactant made by Schill & Seilacher, Germany, having a thickness of 0.3 mm, identified as material "A" in Table 1.

The absorbent core constitutes the comparative example, identified as Option 1 in Table 1 below, where overall six different absorbent core structures are shown, corresponding to Option 1 to Option 6, having different materials for the substrate or first layer 100 and for the cover or second layer 130, characterized by different values of the respective characteristics of Porosity and Permeability for the second or cover layer 130, and of Thickness for the substrate or first layer 100. The layer of absorbent polymer material 110 and the layer of adhesive 120 are the same in all Options. The values of Acquisition, namely the acquisition time after the third gush, and of Rewet, measured according to the respective test methods, are reported in the Table 1 for the absorbent core structures, and show the effect on the final performance of the absorbent core structures of the selection of the component materials according to the present invention.

In Options 2 and 3 the second or cover layer 130 is changed, having Porosity and Permeability values according to the invention, which result in better overall performing structures, as can be seen from the much better Acquisition value of Option 2, with a rather good Rewet, and particularly by the very low Rewet value of Option 3, obtained in combination with a slightly less favourable Acquisition, still definitely better than the Comparative Option 1, which shows the influence of a particularly high Permeability of the second or cover layer 130.

Options 4, 5 and 6 show the effect of varying the characteristics, namely the thickness, of the first or substrate layer 100, in combination with the same second or cover layer 130 of Option 2. It can be noted that Option 6, comprising a thin first or substrate layer 100, although still featuring a fairly good Rewet, has a definitely poor behaviour in terms of Acquisition. Options 4 and 5, instead, have both good Acquisition and Rewet compared to the Comparative Option 1. Particularly Option 5, where the first or substrate layer 100 has a thickness almost corresponding to that of Option 2, although constituted by a different material, shows substantially equivalent values for the Acquisition and the Rewet of the resulting structure, implying the thickness as the relevant parameter for the first or substrate layer 100 of the absorbent ore structure according to the present invention.

TABLE 1

| Option | Cover layer | Substrate layer | Cover Layer Porosity | Cover layer Permeability (Darcy) | Substrate layer Thickness (mm) | Acquisition (sec) | Rewet (g) |
|---|---|---|---|---|---|---|---|
| 1 | A | D | 0.845 | 160.2 | 0.79 | 86 | 0.29 |
| 2 | B | D | 0.874 | 254.6 | 0.79 | 54 | 0.20 |
| 3 | C | D | 0.941 | 330.8 | 0.79 | 76 | 0.04 |
| 4 | B | E | 0.874 | 254.6 | 1.12 | 57 | 0.15 |
| 5 | B | F | 0.874 | 254.6 | 0.76 | 50 | 0.16 |
| 6 | B | G | 0.874 | 254.6 | 0.35 | 123 | 0.19 |

The materials for the cover or second layer 130 and for the substrate or first layer 100 in the various options in Table 1 are as follows.

"A" has been already described above with reference to the comparative Option 1.

"B" is a 12 g/m² spunbond nonwoven constituted by bicomponent 80/20 core/sheath polypropylene/polyethylene fibres, treated with 0.5% by weight Silastol PHP26 surfactant made by Schill & Seilacher, Germany, commercially available from Pegas Nonwovens S.A. under the code 201200010200WW/ZZ.

"C" is a 30 g/m² hydroentangled spunlaced nonwoven comprising PET fibres, available from Ahlstrom Milano s.r.l. under the code MI57422030.

"D" has been already described above with reference to the comparative Option 1.

"E" is an 80 g/m² hybrid bonded, i.e. thermal and latex bonded, air laid material constituted by a homogeneous blend of 80% by weight pulp fibres, 14% by weight of core/sheath 50/50 PP/PE bicomponent fibres and 6% by weight latex, commercially available from Glatfelter USA, formerly Concert Industries Ltd, under the code MH080.102.137.B0999.

"F" is a 95 g/m² airlaid material constituted by a homogeneous blend of 21 g/m² polyethylene powder from Schaetti AG, 46.5 g/m² semi treated EF cellulose pulp from Stora Enso AB, 5.5 g/m² AF192 latex from Air Products, laid onto a 22 g/m² polypropylene nonwoven carrier from Fiberweb plc; the airlaid material is made by Rexcell Tissue & Airlaid AB and is comprised in the absorbent core structure with the carrier side corresponding to the second surface.

"G" is a 30 g/m² airthrough bonded dual layer nonwoven of 50/50 PP/PE core/sheath bicomponent fibres, constituted by a 10 g/m² bottom layer, corresponding to the second surface thereof, of 2 denier, 38 mm long fibres, and of a 20 g/m² top layer, corresponding to the first surface thereof, of 5.2 denier, 38 mm long fibres, available from Tenotex S.p.A. under the trade name Airten Bilayer 1130WZ0114.

The parameters of Permeability and Thickness for the component layers of the absorbent core structure, as well as of Acquisition and Rewet of the overall absorbent core structure of the present invention are measured according to the attached test methods, while the Porosity is calculated according the attached method.

As known to the person skilled in the art, all of the above properties depend on the confining pressure applied onto the sample for the measurement/calculation; the standard confining pressure is intended to be 0.25±0.01 psi if not stated otherwise as this resembles the relevant experimental condition.

Unless stated otherwise, all tests are performed at 23° C.±2° C. and a relative humidity 50%±5%. All samples are conditioned in this environment for twenty four (24) hours before testing.

Thickness

The thickness of a layer of the absorbent core structure according to the present invention, or alternatively of a combinations of layers, for example of an entire absorbent core structure, can be measured with any available method known to the skilled person under the selected confining pressure of 0.25±0.01 psi. For example, the INDA standard test method WSP 120.1 (05) can be used, wherein for the "Thickness testing gage" described under section 5.1, the "applied force", section 5.1.e, is set at 0.25±0.01 psi, and the "Readability", section 5.1.f, has to be 0.01 mm.

Porosity (ε)

Porosity of a specific material constituting the absorbent core structure, is the void volume fraction of the total volume of a material. Depending on the material the porosity may change if the structure is loaded with liquid, for the current invention the porosity is intended calculated for the dry condition. In dry condition Porosity can be easily calculated knowing the composition of the material, the thickness under the desired confining pressure (0.25 psi) and the bulk density of each single component of the material according the following equation.

$$\varepsilon = 1 - \sum_i \frac{BW_i}{\rho_i \cdot B} \quad (E37)$$

Where i is the index counting over all the component, $BW_i$ is the Basis Weight of a specific component, $\rho_i$ is the bulk density of a specific component and B the thickness of the material under the desired confining pressure.

In Plane Radial Permeability (IPRP)

This test is suitable for measurement of the In-Plane Radial Permeability (IPRP) of a porous material. The quantity of a saline solution (0.9% NaCl) flowing radially through an annular sample of the material under constant pressure is measured as a function of time.

Figure 5:
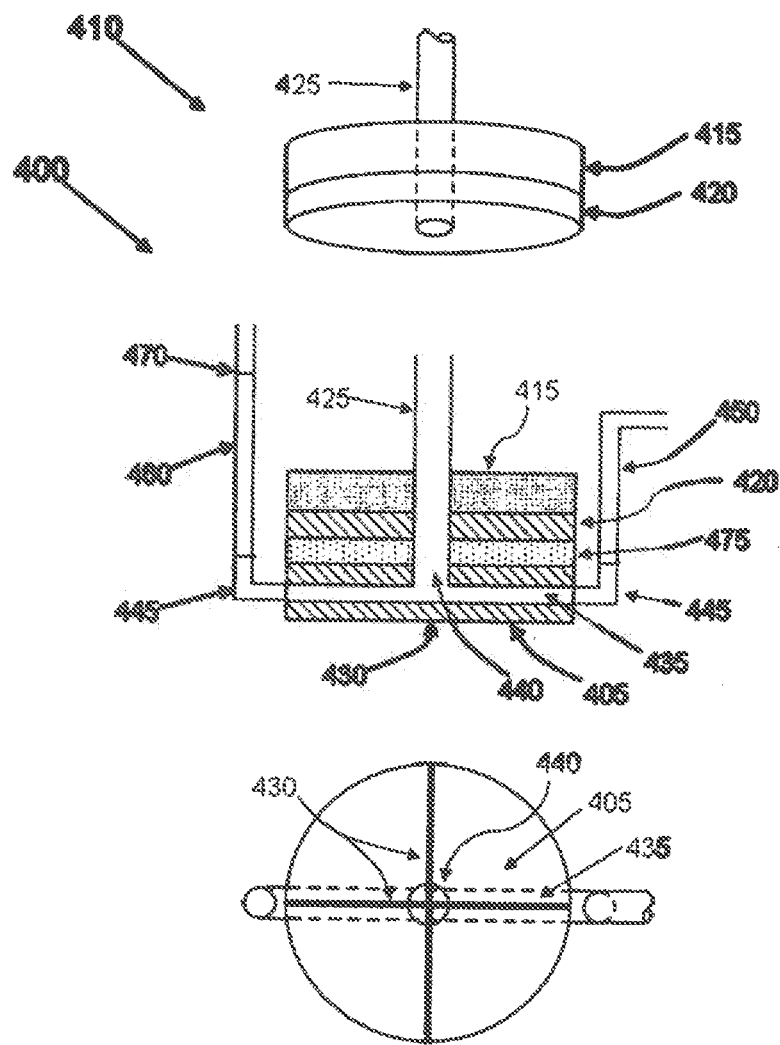
FIGS. 5 and 6 show equipment assemblies used in the In Plane Radial Permeability (IPRP) test described herein.

The IPRP sample holder 400 is shown in FIG. 5 and comprises a cylindrical bottom plate 405, top plate 410, and cylindrical stainless steel weight 415.

Top plate 410 comprises an annular base plate 420 10 mm thick with an outer diameter of 70.0 mm and a tube 425 of 190 mm length fixed at the center thereof. The tube 425 has in outer diameter of 15.8 mm and an inner diameter of 12.0 mm. The tube is adhesively fixed into a circular 12 mm hole in the center of the base plate 420 such that the lower edge of the tube is flush with the lower surface of the base plate, as depicted in FIG. 5. The bottom plate 405 and top plate 410 are fabricated from Lexan® or equivalent. The stainless steel weight 415 has an outer diameter of 70 mm and an inner diameter of 15.9 mm so that the weight is a close sliding fit on tube 425. The thickness of the stainless steel weight 415 is approximately 25 mm and is adjusted so that the total weight of the top plate 410 and the stainless steel weight 415 is 660 g±1 g to provide 1.7 kPa of confining pressure during the measurement.

Bottom plate 405 is approximately 50 mm thick and has two registration grooves 430 cut into the lower surface of the plate such that each groove spans the diameter of the bottom plate and the grooves are perpendicular to each other. Each groove is 1.5 mm wide and 2 mm deep. Bottom plate 405 has a horizontal hole 435 which spans the diameter of the plate. The horizontal hole 435 has a diameter of 11 mm and its central axis is 12 mm below the upper surface of bottom plate 405. Bottom plate 405 also has a central vertical hole 440 which has a diameter of 10 mm and is 8 mm deep. The central hole 440 connects to the horizontal hole 435 to form a T-shaped cavity in the bottom plate 405. The outer portions of the horizontal hole 435 are threaded to accommodate pipe elbows 445 which are attached to the bottom plate 405 in a watertight fashion. One elbow is connected to a vertical transparent tube 460 with a height of 190 mm and an internal diameter of 10 mm. The tube 460 is scribed with a suitable mark 470 at a height of 100 mm above the upper surface of the bottom plate 420. This is the reference for the fluid level to be maintained during the measurement. The other elbow 445 is connected to the fluid delivery reservoir 700 (described below) via a flexible tube.

Figure 6:
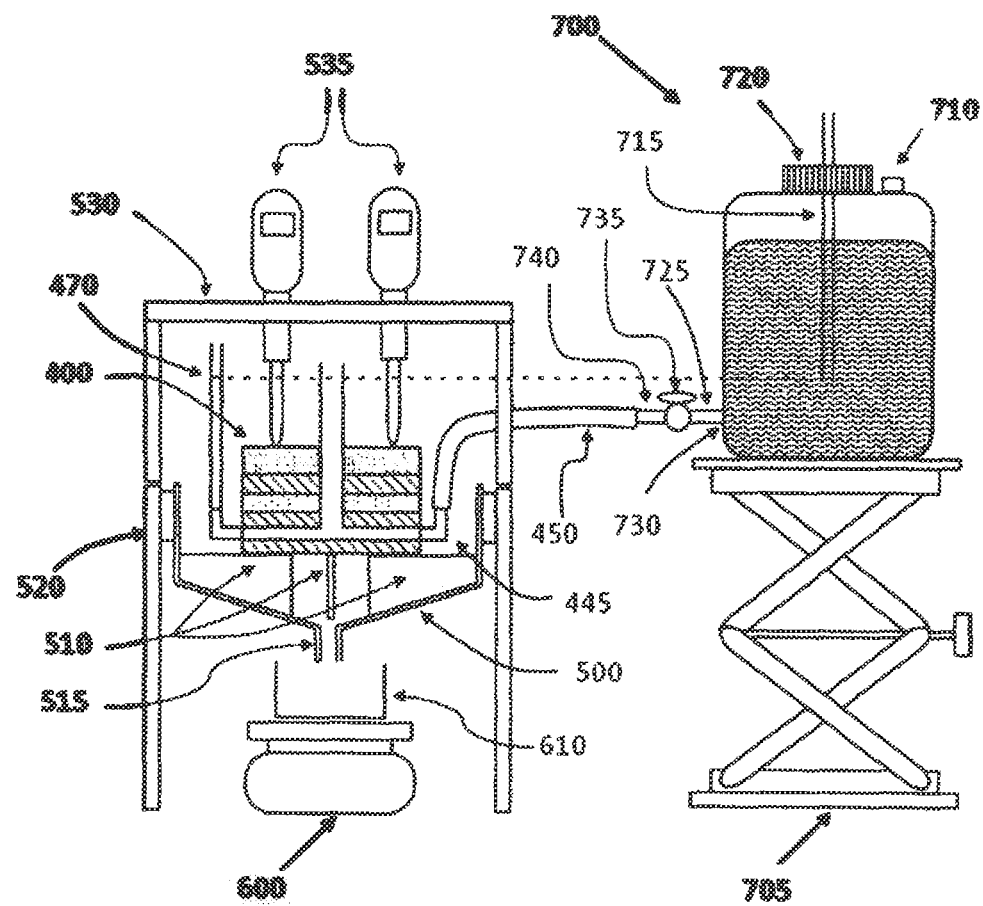

A suitable fluid delivery reservoir 700 is shown in FIG. 6. Reservoir 700 is situated on a suitable laboratory jack 705 and has an air-tight stoppered opening 710 to facilitate filling of the reservoir with fluid. An open-ended glass tube 715 having an inner diameter of 10 mm extends through a port 720 in the top of the reservoir such that there is an airtight seal between the outside of the tube and the reservoir. Reservoir 700 is provided with an L-shaped delivery tube 725 having an inlet 730 that is below the surface of the fluid in the reservoir, a stopcock 735, and an outlet 740. The outlet 740 is connected to elbow 445 via flexible plastic tubing 450 (e.g. Tygon®). The internal diameter of the delivery tube 725, stopcock 735, and flexible plastic tubing 450 enable fluid delivery to the IPRP sample holder 400 at a high enough flow rate to maintain the level of fluid in tube 460 at the scribed mark 470 at all times during the measurement. The reservoir 700 has a capacity of approximately 6 litres, although larger reservoirs may be required depending on the sample thickness and permeability. Other fluid delivery systems may be employed provided that they are able to deliver the fluid to the sample holder 400 and maintain the level of fluid in tube 460 at the scribed mark 470 for the duration of the measurement.

The IPRP catchment funnel 500 is shown in FIG. 6 and comprises an outer housing 505 with an internal diameter at the upper edge of the funnel of approximately 125 mm. Funnel 500 is constructed such that liquid falling into the funnel drains rapidly and freely from spout 515. A stand with horizontal flange 520 around the funnel 500 facilitates mounting the funnel in a horizontal position. Two integral vertical internal ribs 510 span the internal diameter of the funnel and are perpendicular to each other. Each rib 510 s 1.5 mm wide and the top surfaces of the ribs lie in a horizontal plane. The funnel housing 500 and ribs 510 are fabricated from a suitably rigid material such as Lexan® or equivalent in order to support sample holder 400. To facilitate loading of the sample it is advantageous for the height of the ribs to be sufficient to allow the upper surface of the bottom plate 405 to lie above the funnel flange 520 when the bottom plate 405 is located on ribs 510. A bridge 530 is attached to flange 520 in order to mount two digital calipers 535 to measure the relative height of the stainless steel weight 415. The digital calipers 535 have a resolution of ±0.01 mm over a range of 25 mm. A suitable digital caliper is a Mitutoyo model 575-123 (available from McMaster Can Co., catalog no. 19975-A73), or equivalent. Each caliper is interfaced with a computer to allow height readings to be recorded periodically and stored electronically on the computer. Bridge 530 has two circular holes 17 mm in diameter to accommodate tubes 425 and 460 without the tubes touching the bridge.

Funnel 500 is mounted over an electronic balance 600, as shown in FIG. 6. The balance has a resolution of ±0.01 g and a capacity of at least 1000 g. The balance 600 is also interfaced with a computer to allow the balance reading to be recorded periodically and stored electronically on the computer. A suitable balance is Mettler-Toledo model PG5002-S or equivalent. A collection container 610 is situated on the balance pan so that liquid draining from the funnel spout 515 falls directly into the container 610.

The funnel 500 is mounted so that the upper surfaces of ribs 510 lie in a horizontal plane. Balance 600 and container 610 are positioned under the funnel 500 so that liquid draining from the funnel spout 515 falls directly into the container 610. The IPRP sample holder 400 is situated centrally in the funnel 500 with the ribs 510 located in grooves 430. The upper surface of the bottom plate 405 must be perfectly flat and level. The top plate 410 is aligned with and rests on the bottom plate 405. The stainless steel weight 415 surrounds the tube 425 and rests on the top plate 410. Tube 425 extends vertically through the central hole in the bridge 530. Both calipers 535 are mounted firmly to the bridge 530 with the foot resting on a point on the upper surface of the stainless steel weight 415. The calipers are set to zero in this state. The reservoir 700 is filled with 0.9% saline solution and re-sealed. The outlet 740 is connected to elbow 445 via flexible plastic tubing 450.

An annular sample 475 of the material to be tested is cut by suitable means. The sample has an outer diameter of 70 mm and an inner hole diameter of 12mm. One suitable means of cutting the sample is to use a die cutter with sharp concentric blades.

The top plate 410 is lifted enough to insert the sample 475 between the top plate and the bottom plate 405 with the sample centered on the bottom plate and the plates aligned. The stopcock 735 is opened and the level of fluid in tube 460 is set to the scribed mark 470 by adjusting the height of the reservoir 700 using the jack 705 and by adjusting the position of the tube 715 in the reservoir. When the fluid level in the tube 460 is stable at the scribed mark 470 initiate recording data from the balance and calipers by the computer. Balance readings and time elapsed are recorded every 10 seconds for five minutes. The average sample thickness B is calculated from all caliper reading between 60 seconds and 300 seconds and expressed in cm. The flow rate in grams per second is the slope calculated by linear least squares regression fit of the balance reading (dependent variable) at different times (independent variable) considering only the readings between 60 seconds and 300 seconds.

Permeability k (cm$^2$) is then calculated by the following equation:

$$k = \frac{(Q/\rho_1) \cdot \mu \cdot \ln(R_0/R_i)}{2\pi \cdot B \cdot \Delta p} \quad \text{(E47-a)}$$

Where:
k is the permeability (cm$^2$).
Q is the flow rate (g/s).
$\rho_l$ is the liquid density (g/cm$^3$).
μ is the liquid viscosity at 20° C. (Pa*s).

$R_0$ is the outer sample radius (cm).
$R_i$ is the inner sample radius (cm).
B is the average sample thickness (cm)
Δp is the pressure drop (Pa) calculated according to the following Equation E47-b:

$$\Delta p = \left(\Delta h - \frac{B}{2}\right) \cdot g \cdot \rho_1 \cdot 10 \quad \text{(E47-b)}$$

Where:
Δh is the measured liquid hydrostatic pressure (cm)
g is the acceleration constant (m/sec$^2$).
$\rho_l$ is the liquid density (g/cm$^3$).
The permeability is then converted and reported in Darcy
Rewet The rewet method is utilized to assess the dryness of the absorbent core structure with respect to its wearer facing surface, i.e., typically the first surface of the second or cover layer thereof. The test fluid that is utilized for this test is Artificial Menstrual Fluid (AMF).

Apparatus:
1) Blotting Paper available from Whatman (Germany) S & S Rundfilter/Durchmesser 150 mm, No.; 597, Reference-No.: 311812.
2) A weight of 4200 g covered on the lower surface with a foam of moderate flexibility. Both the weight and foam are covered with a thin, flexible plastic film to avoid the foam absorbing fluid. The weight dimensions should allow a 6 cm×10 cm surface to contact the sample under examination. Pressure exerted onto the sample=70 g/cm$^2$.
3) A perspex (7 mm thick) plate of dimensions 6 cm×10 cm with a hole of dimensions 3 cm×4 cm centered in the template.
4) A burette capable of introducing the test fluid at a reproducible rate of 7 ml in 90 seconds.
5) An analytical balance capable of reading to 4 decimal places.

Sample Preparation/Measurement.

A 59 mm×228 mm rectangular sample of the absorbent core structure to be assessed is placed on a flat laboratory surface with the cover layer facing up and centered directly below the burette for test liquid delivery. The perspex plate is positioned on the sample, centered on it, and the AMF test liquid is introduced over the exposed area corresponding to the hole in the perspex plate. After 90 seconds 7 ml of AMF have been introduced to the sample and an electronic counter set to 20 min is activated. During this waiting period a stack of 7 discs of filter paper are weighed on the analytical balance and the weight is recorded.

After 20 min the perspex plate is removed and the stack of filter papers is positioned centrally on the sample being assessed and the weight is gently lowered onto the filter paper stack. The sample and filter paper stack remain under the pressure exerted by the weight for a period of 15 seconds, after which the weight is carefully removed and the filter paper stack is re-weighed. The difference in weight (to the nearest milligram) is recorded as the rewet value. Each test is repeated for at least 5 samples and averaged to ensure adequate accuracy of the measurements.

Acquisition

This procedure measures a product's ability to "keep on absorbing" (acquisition decay) subject to repeated assaults of fluid under a prescribed set of conditions. This method evaluates the time required for the acquisition of given amounts of liquid during repeated imbibitions (three imbibitions of 3 ml each), at relatively high speed (about 3 ml/sec) and under pressure of 1723.7 Pa (0.25 PSI), to model "in use" pressure while wearing.

Each absorbent core structure sample having a rectangular shape 59 mm×228 mm is laid down on a flat surface with the cover layer facing up. A sheet of an apertured formed film is evenly placed onto the sample, with the smoother side facing up; the sheet has a size such that it completely covers the sample. The apertured formed film is a vacuum formed macroscopically expanded three dimensional formed film used as a topsheet in commercial hygienic sanitary articles currently sold in Italy under the trade name Lines Seta, having an open area of about 30%, and is similar to the three dimensional plastic webs described for example in U.S. Pat. No. 4,464,045; it is made of a LDPE/LLDPE blend also containing 0.6% by weight of a surfactant sold under the trade name of Atmer 100. An acquisition plate is placed on the sample and the apertured formed film, centered on the sample. The acquisition plate comprises a rectangular plexiglas plate 70 mm×220 mm×8 mm with an aperture 22 mm in diameter formed in the centre therein. A cylinder 45 mm high and 22 mm in internal diameter is located over the aperture in sealing contact with the plate. The cylinder is filled with Artificial Menstrual Fluid (AMF), and a pressure of 1723.7 Pa (0.25 PSI) is applied to the plate, obtained with appropriate weights positioned on the plate, the pressure being that measured with reference to the portion of the sample under the acquisition plate. The acquisition time is the time from the beginning of each imbibition until the disappearance of the liquid from the interior of the cylinder. A waiting time of 5 minutes is left after each imbibition before repeating the procedure.

The acquisition time after the third imbibition is recorded as the Acquisition of the absorbent core structure of the invention.

Each test is repeated for at least 5 samples and averaged to ensure adequate accuracy of the measurements.

Rheological Creep Test

The Rheological Creep Test mentioned hereinabove for measuring the cohesive strength parameter γ is as described in the copending patent application EP 1447067, assigned to the Procter & Gamble Company.

Preparation of Artificial Menstrual Fluid (AMF)

Artificial Menstrual Fluid is based on modified sheep's blood that has been modified to ensure it closely resembles human menstrual fluid in viscosity, electrical conductivity, surface tension and appearance. It is prepared as explained in U.S. Pat. No. 6,417,424, assigned to The Procter & Gamble Company, from line 33 of column 17 to line 45 of column 18, to which reference is made.

Sample Preparation of Material From an Absorbent Article

When starting from an article comprising the absorbent core structure, in turn comprising the component layers, said layers can be isolated with known means in order to be tested. Typically, in a disposable absorbent article the topsheet can be removed from the backsheet and the absorbent core structure can be separated from any additional layers, if present. For example, the absorbent polymer material can be removed from the substrate layer and the layer of thermoplastic material, e.g. mechanically if possible, or by use of a suitable solvent, in case e.g. the thermoplastic material is a hot melt adhesive. Particles of absorbent polymer material can be hence isolated from other elements of the core e.g., by washing with a suitable solvent which does not interact with the absorbent polymer particles, as can be readily determined by the man skilled in the art. Similarly, the first or substrate layer and the second or cover layer can be isolated, in order to be tested, by carefully separating each layer from the other components of the absorbent core structure, for example mechanically freeing each layer from e.g. adhesive material, or alternatively by washing with a suitable solvent which does not interact with the materials of the respective layers. The solvent is then dried and the layers or the particles of absorbent polymer material can be collected, for example from a plurality of articles of the same type, in the necessary amounts to run the tests.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect of any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent core structure for an absorbent article, the absorbent core structure comprising a first layer,
   the first layer comprising a first layer first surface and a first layer second surface,
   the absorbent core structure further comprising a layer of absorbent polymer material,
   the layer of absorbent polymer material comprising a layer of absorbent polymer material first surface and a layer of absorbent polymer material second surface,
   the absorbent core structure further comprising a layer of adhesive,
   the layer of adhesive comprising a layer of adhesive first surface and a layer of adhesive second surface,
   wherein the layer of absorbent polymer material is comprised between the layer of adhesive and the first layer;
   the layer of absorbent polymer material second surface is facing the first layer first surface;
   and the layer of absorbent polymer material first surface is facing the layer of adhesive second surface,
   the absorbent core structure further comprises a second layer having respective first and second surface, positioned such that the second layer second surface is facing the layer of adhesive first surface
   characterized in that
   the first layer of the absorbent core structure has a thickness of 0.4 mm to 1.5 mm, and the second layer of the absorbent core structure has a Permeability of at least 200 Darcy and a Porosity of at least 0.85;
   wherein the core exhibits an acquisition of less than 80 seconds for a third inhibition.

2. An absorbent core structure according to claim 1, wherein the first layer has a thickness of 0.5 mm to 1.2 mm, the second layer has a Permeability of at least 250 Darcy, and a Porosity of 0.85 to 0.95.

3. An absorbent core structure according to claim 2, wherein the second layer has a Permeability of at least 300 Darcy.

4. An absorbent core structure according to claim 2, wherein the second layer has a Porosity of 0.87 to 0.90.

5. An absorbent core structure according to claim 1, having an overall thickness from 0.5 mm to 2.5 mm 6. An absorbent core structure according to claim 1, having an overall thickness from 1 mm to 2 mm 7. An absorbent core structure according to claim 1, wherein the layer of absorbent polymer material has a basis weight of less than 250 $g/m^2$.

8. An absorbent core structure according to claim 1, wherein the layer of absorbent polymer material has a basis weight of less than 200 $g/m^2$.

9. An absorbent core structure according to claim 1, wherein the layer of absorbent polymer material has a basis weight from 60 $g/m^2$ to 180 $g/m^2$.

10. An absorbent core structure according to claim 1, wherein the layer of absorbent polymer material has a basis weight from 70 $g/m^2$ to 150 $g/m^2$.

11. An absorbent core structure according to claim 1, wherein the first layer has a basis weight of 10 $g/m^2$ to 120 $g/m^2$.

12. An absorbent core structure according to claim 1, wherein the first layer has a basis weight from 20 $g/m^2$ to 100 $g/m^2$.

13. An absorbent core structure according to claim 1, wherein the first layer has a basis weight from 30 $g/m^2$ to about 70 $g/m^2$.

14. An absorbent core structure according to claim 1, wherein the second layer has a basis weight of 10 $g/m^2$ to 80 $g/m^2$.

15. An absorbent core structure according to claim 1, wherein the second layer has a basis weight from 10 $g/m^2$ to 60 $g/m^2$.

16. An absorbent core structure according to claim 1, wherein the second layer has a basis weight from 20 $g/m^2$ to 40 $g/m^2$.

17. An absorbent core structure according to claim 1, wherein the adhesive is a hot melt adhesive.

18. An absorbent core structure according to claim 1, wherein the adhesive is fiberized, comprising fibres having an average thickness from 1 μm to 100 μm and an average length from 5 mm to 50 cm.

19. An absorbent core structure according to claim 18, wherein the fibres have an average thickness from 25 μm to 75 μm.

20. An absorbent core structure according to claim 1, wherein the adhesive is provided in a basis weight of from 11 $g/m^2$ to 3 $g/m^2$.

21. An absorbent core structure according to claim 1, wherein the adhesive is provided in a basis weight from 9 $g/m^2$ to 5 $g/m^2$.

22. An absorbent core structure according to claim 1, wherein the layer of absorbent polymer material second surface is in contact with the first layer first surface;
the layer of absorbent polymer material first surface is in contact with the layer of adhesive second surface;
the second layer second surface is in contact with the layer of adhesive first surface.

23. An absorbent feminine hygiene product comprising the absorbent core structure according to claim 1.

24. The absorbent feminine hygiene product according to claim 23, wherein the absorbent feminine hygiene product is a sanitary napkin.

* * * * *